United States Patent
Dong et al.

(10) Patent No.: US 11,634,739 B2
(45) Date of Patent: Apr. 25, 2023

(54) REGULATION METHOD FOR PREPARING γ-POLYGLUTAMIC ACID BY SLUDGE SUBSTRATE FERMENTATION

(71) Applicant: Tongji University, Shanghai (CN)

(72) Inventors: Bin Dong, Shanghai (CN); Xin Li, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 73 days.

(21) Appl. No.: 17/027,732

(22) Filed: Sep. 22, 2020

(65) Prior Publication Data

US 2022/0033866 A1    Feb. 3, 2022

(30) Foreign Application Priority Data

Jul. 30, 2020    (CN) .......................... 202010751294.7

(51) Int. Cl.
| | | |
|---|---|---|
| *C12P 13/02* | (2006.01) | |
| *C08G 69/08* | (2006.01) | |
| *C12N 1/20* | (2006.01) | |
| *C12R 1/07* | (2006.01) | |

(52) U.S. Cl.
CPC .............. *C12P 13/02* (2013.01); *C08G 69/08* (2013.01); *C12N 1/205* (2021.05); *C12R 2001/07* (2021.05)

(58) Field of Classification Search
CPC ......... C12P 13/02; C08G 69/08; C08G 69/04; C08G 69/10; C12N 1/205; C12R 2001/07
See application file for complete search history.

(56) References Cited

FOREIGN PATENT DOCUMENTS

| CN | 106282253 | * | 1/2017 |
| CN | 106947724 | * | 7/2017 |

OTHER PUBLICATIONS

Zhang et al., Waste Biomass Valor 10:789-795, published online Oct. 7, 2017.*
Zhang et al., Water 10, 545, pp. 1-20, published online Apr. 25, 2018.*
Sirisansaneeyakul et al. World J Microbiol Biotechnol 33, 173, pp. 1-8, 2017.*
Shi et al., Biotechnology and Bioprocess Engineering 11:251-257, 2006.*
Ogunleye et al., Microbiology 161:1-17, 2015.*

* cited by examiner

*Primary Examiner* — Delia M Ramirez
(74) *Attorney, Agent, or Firm* — Bayramoglu Law Offices LLC

(57) ABSTRACT

A regulation method for preparing γ-polyglutamic acid by sludge substrate fermentation includes: 1) extraction of glutamic acid from sludge protein (high pressure hydrothermal treatment, gravity pressure filtration treatment), 2) secondary metabolic synthesis of γ-polyglutamic acid (activation of domesticated strains and secondary metabolic fermentation strains); and 3) preparation of pure γ-polyglutamic acid (acidification, centrifugation, filtration, precipitation based on polar repulsion, purification, impurity removal and drying). The present invention realizes a recycling of high-value carbon and nitrogen sources of sludge without secondary pollution, and has advantages of simplified operation, good feasibility, and low preparation cost. The synthesized γ-polyglutamic acid has high economic value and broad application prospect.

9 Claims, 1 Drawing Sheet

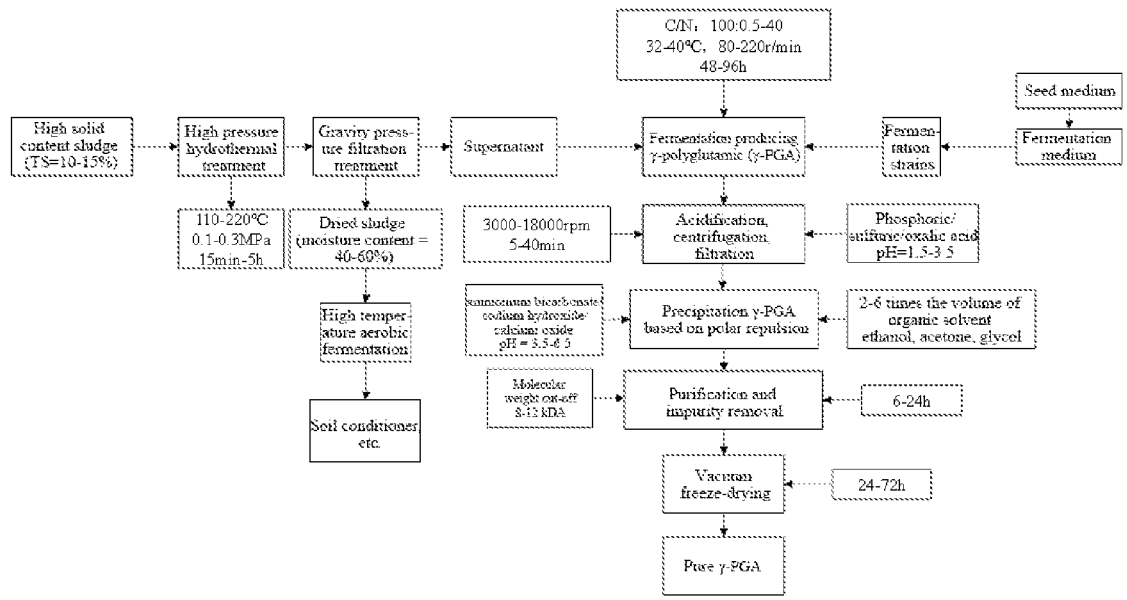

REGULATION METHOD FOR PREPARING γ-POLYGLUTAMIC ACID BY SLUDGE SUBSTRATE FERMENTATION

CROSS REFERENCE TO THE RELATED APPLICATIONS

This application is based upon and claims priority to Chinese Patent Application No. 202010751294.7, filed on Jul. 30, 2020, the entire contents of which are incorporated herein by reference.

TECHNICAL FIELD

The present invention relates to the technical field of organic solid waste treatment and resource utilization, and in particular, to a regulation method for preparing γ-polyglutamic acid by sludge substrate fermentation.

BACKGROUND

In a common secondary sewage treatment plant, sludge treatment accounts for about 30-40% of a total investment. It is predicted that a total sludge production in 2020 will reach 70 million tons (based on 80% water content) in China. In face of such high sludge production, landfill or incineration after sludge digestion has become a common disposal method. As the more economical method, Landfill has been the main solution, but it is not an ideal solution as a landfill occupies large area of spaces, and has potential risks of groundwater secondary pollution. Therefore, sludge resource utilization or efficient treatment methods have become a research hotspot in China and even around the world.

γ-polyglutamic acid (γ-PGA) is an extracellular polymer produced by microbial fermentation of glutamic acid. It is a water-soluble and biodegradable new polymer material and has broad application prospects in environmental protection, chemical industry and other fields. Currently, fermentation technology adopts fermentation medium synthesized by natto, dipotassium hydrogen phosphate and other substances, which leads to a high cost of fermentation medium. In addition, there are many problems in traditional purification methods, such as difficulty associated with removing inorganic salts produced in traditional purification process, and high price associated with ultrafiltration and osmotic purification. For the reasons stated above, the cost of γ-polyglutamic acid is high, which makes it less competitive in the market.

Sludge is a kind of organic waste with high protein content (the protein accounts for 60-80% of organic matter content), and amino acids contained in sludge are mainly alanine (ALA) and glutamic acid (Glu), which can reach 20-30% of total amino acids, this provides a possibility to produce polyglutamic acid using sludge as a cheap substrate for fermenting. However, the sludge has complex compositions. How to ensure that microorganisms can use glutamic acid in sludge protein to perform secondary metabolism to produce γ-PGA, how to change the situation where a large amount of inorganic salts is brought by adjusting pH in a traditional purification method, and how to ensure a feasibility of process and economic benefits have become the crux of the matter.

SUMMARY

The technical problem to be solved by the present invention is, in view of the technical status described above, to provide a regulation method for preparing γ-polyglutamic acid by sludge substrate fermentation, which has advantages of low preparation cost, simple operation and stable product quality.

The technical scheme adopted by the present invention to solve the above technical problem is as follows:

A regulation method for preparing γ-polyglutamic acid by sludge substrate fermentation, the method includes the following steps.

1) Extraction of Glutamic Acid from Sludge Protein:

A. pretreatment: putting a sludge with a solid content of $10\%-15\%$ into a high-pressure reactor for a pretreatment to obtain a sludge slurry;

B. gravity pressure filtration treatment; performing a gravity pressure filtration on the sludge slurry obtained in step A through a filter press, to obtain a dried sludge with a moisture content of 40%-60% and a supernatant, keeping the supernatant, and recycling the dried sludge after a harmless treatment:

2) Synthesis of γ-Polyglutamic Acid by Secondary Metabolism:

C. activation of domesticated strains: using a standard *Bacillus* seed medium to activate and cultivate fermentation strains, and then using a fermentation medium added with fermentation raw materials to domesticate and cultivate the fermentation strains, to amplify and propagate the fermentation strains to a maximum value, and obtaining activated and domesticated *Bacillus*;

D. secondary metabolic fermentation: inoculating the activated and domesticated *Bacillus* obtained from step C into the supernatant of step B, performing a proper ventilation to ensure sufficient oxygen supply, and adjusting fermentation conditions to obtain a fermentation product containing γ-polyglutamic acid;

3) Preparation of Pure γ-Polyglutamic Acid:

E. acidification, centrifugation and filtration: acidifying the fermentation product obtained in step D to adjust the pH level to precipitate strains and polysaccharides, followed by centrifugation, filtering and collecting a supernatant;

F. precipitation based on polar repulsion: restoring the pH level of the supernatant obtained in step E and using organic solvents with repellent polar to precipitate the γ-polyglutamic acid, and collecting a precipitation by centrifugation:

G. purification and impurity removal: dissolving the precipitation obtained in step F in deionized water to obtain a γ-polyglutamic acid solution, dialyzing at 4° C. for 6 h-24 h, removing small molecular organic substances and inorganic salt impurities by a dialysis bag with a molecular weight cut-off of 8-12 kDa to obtain a dialysate;

H. drying: performing a vacuum freeze-drying on the dialysate obtained in G for 24-72 h to obtain pure γ-polyglutamic acid.

In order to optimize the above technical scheme, the method further includes:

Pretreatment conditions in step A are as follows: temperature is controlled at 110° C.-220° C., the intensity of pressure is 0.1 MPa-0.3 MPa, and the time is 15 min-5 hr.

In step C mentioned above, the carbon/nitrogen (C/N) ratio of strain amplification and propagation is set as 100: 0.5-5, the temperature is controlled at 25° C.-32° C., the pH level is 6.8-7.2, and the culture time is 24 hr-72 hr.

*Bacillus* used in step C mentioned above is *Bacillus subtilis, Bacillus natto, Bacillus amyloliquefaciens, Bacilluslichenuformis*, and one of their domesticated strains producing the γ-polyglutamic acid.

Conditions for secondary metabolism in the above step D are set as follows: the C/N ratio is set as 100:5-40, the temperature is controlled at 32° C.-40° C., the pH level is 5.5-8.5, the rotation speed is set as 80 r/min-220 r/min, and the fermentation time is 48 hr-96 hr.

In the above-mentioned step E, the pH level is adjusted to 1.5-3.5 with an acid solution, the rotational speed of the centrifugation is 3000 rpm-18000 rpm, and the centrifuge time is 5 min-40 min, the supernatant is separated and collected.

The acid solution is phosphoric acid, oxalic acid or sulfuric acid.

In the above step F, the pH level is first adjusted to 3.5-6.5 with an alkaline solution, followed by precipitating the γ-polyglutamic acid by using an organic solvent which is concentrated by 2-6 times in volume with repellent polar; centrifugation is performed at 8000 rpm-15000 rpm for 5 min-40 min to separate and collect the precipitate.

The alkaline solution is ammonium bicarbonate, sodium hydroxide or calcium oxide, and the organic solvent with repellent polar is at least one selected from the group consisting of ethanol, acetone and glycol.

When the organic solvent with repellent polar is two selected from the group consisting of ethanol, acetone and glycol, the mixing ratio is 1:0.1-20; when ethanol, acetone and glycol are all selected for mixing, the mixing ratio is 1:1-15:6-30.

Compared with the prior art, the regulation method for preparing γ-polyglutamic acid by sludge substrate fermentation has the following advantages:

(1) about 42-50 kg sludge (based on 85% water content) can be used to produce 1 kg highly pure product (>95%) γ-polyglutamic acid. At the same time, sludge as an organic waste, which has a large output, and its treatment and disposal have always been a difficult problem at home and abroad, which provides a huge amount of free fermentation substrate for the present invention to solve the problem of high price of fermentation substrate in the current technology;

(2) changes the traditional acid-base regulating agent, improves the problem of excessive inorganic salt impurities introduced in a purification process of the current technology, reduces dialysis times, results in simplified operations and diminishes an overall cost;

(3) only uses organic solvents with repellent polar to precipitate γ-polyglutamic acid, which can be recycled by reduced pressure distillation, and only 1-2 L of the organic solvents with repellent polar is needed to purify 1-3 kg of the supernatant each time; and (4) greatly reduces the cost of preparing pure γ-polyglutamic acid, which is about 60-100 yuan per kilogram according to the present invention, and the finished product can reach a standard of agricultural grade γ-polyglutamic acid. Note, the price of polyglutamic acid in the market is generally more than 150 yuan/kg.

BRIEF DESCRIPTION OF THE DRAWINGS

FIG. 1s a flow chart showing the process of the present invention.

DETAILED DESCRIPTION OF THE EMBODIMENTS

The present invention is described in detail in combination with the accompanying drawings and embodiments.

As shown in the FIGURE, a regulation method for preparing γ-polyglutamic acid by sludge substrate fermentation includes the following steps:

1) Extraction of Glutamic Acid from Sludge Protein

A. pretreatment: a sludge with a solid content of 10%-15% is put into a high-pressure reactor for a pretreatment to obtain a sludge slurry; pretreatment conditions are as follows: temperature is controlled at 110° C.-220° C., intensity of pressure is 0.1 MPa-0.3 MPa, and the pretreatment time is 15 min-5 hr.

B. gravity pressure filtration treatment: the sludge slurry obtained in step A is subjected to a gravity pressure filtration through a filter press, to obtain a dried sludge with a moisture content of 40%-60% and a supernatant, the supernatant is retained, and the dried sludge is recycled after a harmless treatment (e.g., aerobic fermentation, etc.); the dried sludge can be used as a soil conditioner after recycling.

2) Synthesis of γ-Polyglutamic Acid by Secondary Metabolism

C. activation of domesticated strains: a standard *Bacillus* seed medium is used to activate and cultivate fermentation strains, and then a fermentation medium mixed with fermentation raw materials is used to domesticate and cultivate the fermentation strains, the fermentation strains are amplified and propagated to a maximum value, and activated and domesticated *Bacillus* is obtained; the C/N ratio of strain amplification and propagation is set as 100:0.5-5, the temperature is controlled at 25° C.-32° C., the pH level is 6.8-7.2, and the culture time is 24 hr-72 hr; *Bacillus* used is *Bacillus subtilis, Bacillus natto, Bacillus amyloliquefaciens, Bacillus licheniformis*, and one of their domesticated strains producing γ-polyglutamic acid.

D. secondary metabolic fermentation: the supernatant of step B is inoculated with the activated and domesticated *Bacillus* obtained from step C, proper ventilation is performed to ensure sufficient oxygen supply, and fermentation conditions are adjusted to obtain a fermentation product containing the γ-polyglutamic acid; conditions for secondary metabolism are set as follows: the C/N ratio is set as 100:5-40, the temperature is controlled at 32° C.-40° C., the pH level is 5.5-8.5, the rotation speed is set as 80 r/min-220 r/min, and the fermentation time is 48 hr-96 hr.

3) Preparation of Pure γ-Polyglutamic Acid

E. acidification, centrifugation and filtration: the fermentation product obtained in step D is acidified to adjust the pH level to precipitate strains and polysaccharides, and then a supernatant is collected after centrifugation and filtration; acidified adjustment is to adjust the pH level to 1.5-3.5 with an acid solution, the rotational speed of the centrifugation is 3000 rpm-18000 rpm, and the time is 5 min-40 min, and the supernatant is separated and collected; the acid solution is phosphoric acid, oxalic acid or sulfuric acid.

F. precipitation based on polar repulsion: the pH level of the supernatant obtained in step E is restored, and an organic solvent with repellent polar is used to precipitate the γ-polyglutamic acid, and a precipitation obtained by centrifugation is collected; the pH level is adjusted back to 3.5-6.5 with an alkaline solution, and then γ-polyglutamic acid is precipitated by using an organic solvent, which is concentrated by 2-6 times in volume with repellent polar; the precipitation is separated and collected after centrifugation at a rotational speed of 8000 rpm-15000 rpm for 5 min-40 min; the alkaline solution is ammonium bicarbonate, sodium hydroxide or calcium oxide, and the organic solvent with repellent polar is at least one selected from the group consisting of ethanol, acetone and glycol, when the organic solvent with repellent polar is two selected from the group consisting of ethanol, acetone and glycol, the mixing ratio is 1:0.1-20; when ethanol, acetone and glycol are all selected for mixing, the mixing ratio is 1:1-15:6-30.

G. purification and impurity removal: the precipitation obtained in step F is dissolved in deionized water to obtain a γ-polyglutamic acid solution, which is dialyzed at 4° C. for 6 hr-24 hr, a dialysate is obtained by removing small molecular organic substances and inorganic salt impurities using a dialysis bag with a molecular weight cut-off of 8-12 kDa;

H. drying: the dialysate obtained in step G is subjected to a vacuum freeze-drying for 24-72 h to obtain pure γ-polyglutamic acid.

The preparation method of the γ-polyglutamic acid of the present invention is further described through a specific embodiment:

Embodiment: fermentation with *Bacillus subtilis*, the specific steps are as follows;

1) Extraction of Glutamic Acid from Sludge Protein

A. pretreatment: a sludge (with a solid content of 15%) is put into a high-pressure reactor for a pretreatment to obtain a sludge slurry, temperature is controlled at 170° C., intensity of pressure is 0.2 MPa, and the pretreatment time is 4 hr;

B. gravity pressure filtration treatment; the sludge slurry obtained in step A is subjected to a gravity pressure filtration through a filter press to obtain a dried sludge (moisture content of 55%) and a supernatant, the supernatant is retained, and the dried sludge is recycled after a harmless treatment such as an aerobic fermentation;

2) Synthesis of γ-Polyglutamic Acid by Secondary Metabolism

C. activation of domesticated strains: a standard *Bacillus subtilis* seed medium is used to activate and cultivate fermentation strains, and then a fermentation medium mixed with fermentation raw materials is used to domesticate and cultivate *Bacillus subtilis*; the C/N ratio of strain amplification and propagation is set as 100:0.5, the temperature is controlled at 30° C., the pH level is 7.2, and the culture time is 42 hr; then activated and domesticated *Bacillus subtilis* is obtained.

D. secondary metabolic fermentation: the supernatant of step B is inoculated with the activated and domesticated *Bacillus subtilis* obtained from step C, proper ventilation is performed to ensure sufficient oxygen supply, and fermentation conditions are adjusted to obtain a fermentation product containing the γ-polyglutamic acid; the C/N ratio is set as 100:5, the temperature is controlled at 37° C., the pH level is 7.5, the rotation speed is 220 r/min, and the fermentation time is 48 hr;

3) Preparation of Pure γ-Polyglutamic Acid

E. acidification, centrifugation and filtration: the fermentation product obtained in step D is adjusted to a pH level of 1.5 with sulfuric acid to precipitate strains and polysaccharides, the rotational speed of the centrifugation is 18000 rpm, and the time is 20 min, and the supernatant is separated and collected;

F. precipitation based on polar repulsion: the supernatant obtained in step E is adjusted to a pH level of 6 with ammonium bicarbonate, then γ-polyglutamic acid is precipitated by using ethanol concentrated by 6 times in volume; the precipitation is separated and collected after centrifugation at a rotational speed of 15000 rpm for 40 min;

G. purification and impurity removal: the precipitation obtained in step F is dissolved in deionized water to obtain a γ-polyglutamic acid solution, which is dialyzed at 4° C. for 24 h, a dialysate is obtained by removing small molecular organic substances and inorganic salt impurities using a dialysis bag with a molecular weight cut-off of 10 kDa;

H. drying: the dialysate obtained in step G is subjected to a vacuum freeze-drying for 24 hr to obtain pure γ-polyglutamic acid.

The optimal embodiment of the present invention has been disclosed, and all different variations or modifications made by those having ordinary skills in the art will not be out of the scope of the present invention.

What is claimed is:

1. A regulation method for preparing γ-polyglutamic acid from sludge, comprising the steps of:
   (a) extraction of glutamic acid from the sludge by
      (i) pretreating the sludge with a solid content of 10%-15% in a high-pressure reactor to obtain a sludge slurry, wherein pretreating the sludge in the high-pressure reactor comprises pretreating at a temperature of 110° C.-220° C. in the reactor and a pressure of 0.2 MPa or 0.3 MPa in the reactor for 4-5 hr; and
      (ii) performing gravity pressure filtration on the sludge slurry obtained in step (a)(i) through a filter press to obtain a dried sludge with a moisture content of 40%-60% and a first supernatant, keeping the first supernatant, and recycling the dried sludge;
   (b) synthesis of the γ-polyglutamic acid by
      (i) mixing a standard *Bacillus* culture medium comprising a *Bacillus* strain and a fermentation medium comprising fermentation raw materials to obtain cultivated *Bacillus*; and
      (ii) inoculating the cultivated *Bacillus* obtained from step (b)(i) into the first supernatant of step (a)(ii), performing aeration of the inoculated first supernatant to ensure a sufficient oxygen supply, and adjusting fermentation conditions of the inoculated first supernatant to obtain a fermentation product containing the γ-polyglutamic acid; and
   (c) preparing pure γ-polyglutamic acid by
      (i) acidifying the fermentation product containing the γ-polyglutamic acid obtained in step (b)(ii) to adjust the fermentation product pH to precipitate cell mass and polysaccharides, centrifugation to separate the precipitated cell mass and polysaccharides, and collecting a second supernatant from the first centrifugation;
      (ii) adjusting the pH of the second supernatant obtained in step (c)(i) with an alkaline solution and using an organic solvent to precipitate the γ-polyglutamic acid, and a second centrifugation to isolate the precipitated γ-polyglutamic acid;
      (iii) dissolving the precipitated γ-polyglutamic acid obtained in step (c)(ii) in deionized water to obtain a γ-polyglutamic acid solution, dialyzing the γ-polyglutamic acid solution at 4° C. for 6-24 hr, removing small molecular organic substances and inorganic salt impurities by a dialysis bag with a molecular weight cut-off of 8-12 kDa to obtain a dialyzed γ-polyglutamic acid solution; and
      (iv) vacuum freeze-drying the dialyzed γ-polyglutamic acid solution obtained in step (c)(iii) for 24-72 hr to obtain the pure γ-polyglutamic acid.

2. The regulation method according to claim 1, wherein in step (b)(i), the temperature is controlled at 25° C.-32° C., the pH of the fermentation medium is 6.8-7.2, and the culture time is 24 hr-72 hr.

3. The regulation method according to claim 2, wherein the *Bacillus* strain used in the standard *Bacillus* culture medium of step (b)(i) is one selected from the group consisting of *Bacillus subtilis*, *Bacillus natto*, *Bacillus amyloliquefaciens*, and *Bacillus licheniformis*.

4. The regulation method according to claim 1, wherein in step (b)(ii) the temperature is controlled at 32° C.-40° C., the pH is 5.5-8.5, and the fermentation time is 48 hr-96 hr.

5. The regulation method according to claim 1, wherein in step (c)(i), the pH of the fermentation product is adjusted to 1.5-3.5 with an acid solution, and the first centrifugation is carried out at 3000-18000 rpm for 5-40 min.

6. The regulation method according to claim 5, wherein the acid solution is selected from the group consisting of a phosphoric acid solution, an oxalic acid solution and a sulfuric acid solution.

7. The regulation method according to claim 1, wherein in step (c)(ii), the pH of the second supernatant is adjusted to 3.5-6.5 with the alkaline solution, wherein the γ-polyglutamic acid is precipitated by using the organic solvent, and wherein the second centrifugation is performed at 8000-15000 rpm for 5-40 min to separate and collect the precipitated γ-polyglutamic acid.

8. The regulation method according to claim 7, wherein the alkaline solution is selected from the group consisting of an ammonium bicarbonate solution, a sodium hydroxide solution and a calcium oxide solution, and the organic solvent comprises at least one solvent selected from the group consisting of ethanol, acetone and glycol.

9. The regulation method according to claim 8, wherein when the organic solvent comprises two solvents selected from the group consisting of ethanol, acetone and glycol.

* * * * *